United States Patent
Menon et al.

(10) Patent No.: US 12,409,266 B2
(45) Date of Patent: Sep. 9, 2025

(54) CONVERGENT-DIVERGENT DRIP CHAMBER INTEGRATED WITH FLOATING VALVE MEMBER

(71) Applicant: CareFusion 303, Inc., San Diego, CA (US)

(72) Inventors: Kanjimpuredathil Muralikrishna Menon, Bangalore (IN); Aman Agarwal, Bangalore (IN); Rahul Puthukkad, Bengaluru (IN); Arjun Murali, Kochi (IN)

(73) Assignee: CAREFUSION 303, INC., San Diego, CA (US)

( * ) Notice: Subject to any disclaimer, the term of this patent is extended or adjusted under 35 U.S.C. 154(b) by 1171 days.

(21) Appl. No.: 17/085,803

(22) Filed: Oct. 30, 2020

(65) Prior Publication Data

US 2022/0133983 A1   May 5, 2022

(51) Int. Cl.
*A61M 5/14*      (2006.01)
*A61M 5/168*    (2006.01)
*A61M 5/40*      (2006.01)

(52) U.S. Cl.
CPC ...... *A61M 5/1411* (2013.01); *A61M 5/16881* (2013.01); *A61M 5/40* (2013.01)

(58) Field of Classification Search
CPC .. A61M 5/1411; A61M 5/16881; A61M 5/40; A61M 2039/248; A61M 39/227; A61M 39/24; A61M 5/1408; A61M 5/1412; A61M 5/1413; A61M 5/16827; A61M 5/16877
See application file for complete search history.

(56) References Cited

U.S. PATENT DOCUMENTS

| | | | |
|---|---|---|---|
| 4,055,176 A | * | 10/1977 | Lundquist ............ A61M 5/1411 604/254 |
| 4,175,558 A | | 11/1979 | Hess, III et al. |
| 4,606,365 A | | 8/1986 | Siposs |
| 4,640,307 A | | 2/1987 | Roberts |
| 5,527,295 A | | 6/1996 | Wing |

(Continued)

FOREIGN PATENT DOCUMENTS

| | | |
|---|---|---|
| CA | 616602 A | 3/1961 |
| CA | 1130161 A | 8/1982 |

(Continued)

OTHER PUBLICATIONS

International Search Report and Written Opinion for Application No. PCT/US2021/057034, dated Feb. 18, 2022, 15 pages.

(Continued)

*Primary Examiner* — Theodore J Stigell

(74) *Attorney, Agent, or Firm* — MASCHOFF BRENNAN

(57) ABSTRACT

A drip chamber device may include a housing including an inlet and an outlet disposed downstream of the inlet, and a chamber defined by an inner circumferential surface of the housing. The chamber may fluidly connect the inlet with the outlet. A valve member may be disposed in the chamber to move between (i) a closed state where fluid communication between the inlet and the chamber is blocked, and (ii) an open state where fluid communication between the inlet and the chamber is not blocked, based on a level of fluid within the chamber.

20 Claims, 3 Drawing Sheets

(56) References Cited

U.S. PATENT DOCUMENTS

| | | | |
|---|---|---|---|
| 6,261,267 | B1 | 7/2001 | Chen |
| 6,502,461 | B2 | 1/2003 | Keller |
| 6,508,120 | B2 | 1/2003 | Yekutiely et al. |
| 8,596,119 | B2 | 12/2013 | Teli et al. |

FOREIGN PATENT DOCUMENTS

| | | | | |
|---|---|---|---|---|
| CN | 208220721 | U | | 12/2018 |
| CN | 111727382 | A | | 9/2020 |
| CN | 216934261 | U | | 7/2022 |
| DE | 2919343 | A1 | | 11/1980 |
| GB | 2028975 | A | * | 3/1980 |
| GB | 2030466 | A | | 4/1980 |
| JP | S5532579 | A | | 3/1980 |
| JP | H09117505 | A | | 5/1997 |
| JP | 2004337364 | A | | 12/2004 |

OTHER PUBLICATIONS

Japanese Office Action for Application No. 2023-520032, dated Mar. 28, 2025, 7 pages including translation.
Chinese Office Action for Application No. 202111255704.X, dated Jun. 24, 2025, 18 pages including translation.

* cited by examiner

CONVERGENT-DIVERGENT DRIP CHAMBER INTEGRATED WITH FLOATING VALVE MEMBER

TECHNICAL FIELD

The present disclosure generally relates to medical fluid connectors, and in particular to a flow control drip chamber connector having a valve member capable of preventing under-infusion in intravenous ("IV") sets with a secondary line, as well as preventing backflow of secondary drug into the primary IV fluid bag.

BACKGROUND

Infusion IV sets are generally used in infusion therapy in order to deliver medication from a pre-filled container, e.g., an IV bottle or bag containing the desired medication, to a patient. Generally, the IV tubing is connected to a catheter and inserted into the localized area to be treated. In some cases, there is a need to deliver multiple medications to the patient in potentially differing dosages, thereby causing the need for an IV extension set having multiple branches of tubing or fluid lines through which the multiple medications may be dispensed to the patient.

Medical infusion therapy involves the administration of medication through a needle or catheter. The medication may be administered using intravenous, intramuscular, or epidural techniques. Typically, infusion therapy includes a fluid source coupled through tubing to a patient's intravenous needle or a catheter. The fluid, which may comprise medication or any other fluid, is usually dripped from the fluid source, through a fluid pathway, and into the patient. Typically, a primary fluid source and one or more secondary fluid sources may be joined to the fluid pathway between the source and the patient.

The primary and secondary fluid sources may be joined in the fluid pathway such that the secondary fluid may be delivered concurrently with the primary fluid. Alternatively, flow of the primary fluid may be halted where the pressure head at the secondary fluid source is greater than that at the primary fluid source, thereby allowing delivery of the secondary fluid. Delivery of the primary fluid may then be restarted after flow of the secondary fluid has ceased.

During infusion with IV sets, a secondary drug feed could potentially flow backwards into primary IV line leading to under infusion of the secondary drug. Though a check valve may be positioned in the primary line to prevent backflow, check valves are prone to failure. Some common reasons for check valve failure are due to debris existing in infusates and minimal pressure differential at the back check valve affecting its performance.

The description provided in the background section should not be assumed to be prior art merely because it is mentioned in or associated with the background section. The background section may include information that describes one or more aspects of the subject technology.

SUMMARY

In accordance with various embodiments of the present disclosure, a drip chamber device may include a housing including an inlet and an outlet disposed downstream of the inlet, and a chamber defined by an inner circumferential surface of the housing. The chamber may fluidly connect the inlet with the outlet. A valve member may be disposed in the chamber to move between (i) a closed state where fluid communication between the inlet and the chamber is blocked, and (ii) an open state where fluid communication between the inlet and the chamber is not blocked, based on a level of fluid within the chamber.

In accordance with various embodiments of the present disclosure, a drip chamber device may include a housing having a top end including an inlet for receiving a primary fluid, an opposing bottom end including an outlet for dispensing fluid from the housing, an intermediate section between the top and bottom ends, and a sidewall having (i) a first portion extending radially outward from the top end to the intermediate section of the housing, and (ii) a second portion extending radially inward from the intermediate section to the bottom end of the housing. An inner circumferential surface of the sidewall may define a chamber. The drip chamber device may further include a sealing ring circumferentially disposed along the inner circumferential surface, and a valve member moveably disposed in the chamber. The valve member may be displaceable in a proximal direction into the sealing ring by a buoyant force when fluid level in the chamber exceeds a predetermined level.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to flow control devices, and more particularly to flow control devices having a valve member capable of preventing under infusion in IV sets with a secondary fluid line, as well as preventing backflow of drug from the secondary fluid line into the primary fluid line.

IV sets with a secondary fluid line tend to experience under infusion of the secondary drug due to backflow of the secondary drug into the primary line resulting from failure of the check valve in the primary fluid line. The most frequent causes of failure of the check valve are due to debris accumulated at the time of spiking and seeping of drug in the secondary fluid line into the primary fluid line at low pressures. A common cause of under-infusion is dilution of drug at the time of back priming of the secondary IV and also at the time of equal head in the primary and secondary fluid lines. Other causes include dead volume in the secondary fluid line, as well as time taken to infuse the drug. The drip chamber devices of the various embodiments described herein overcome the above issues commonly associated with IV sets having primary and secondary fluid lines. In particular, various embodiments of the present disclosure are directed to providing a drip chamber device that prevents backflow of secondary drug into the primary fluid line. When head heights at the primary fluid source and the secondary fluid source are equal, both primary and secondary fluids may be delivered in equal proportion.

Figure 1:
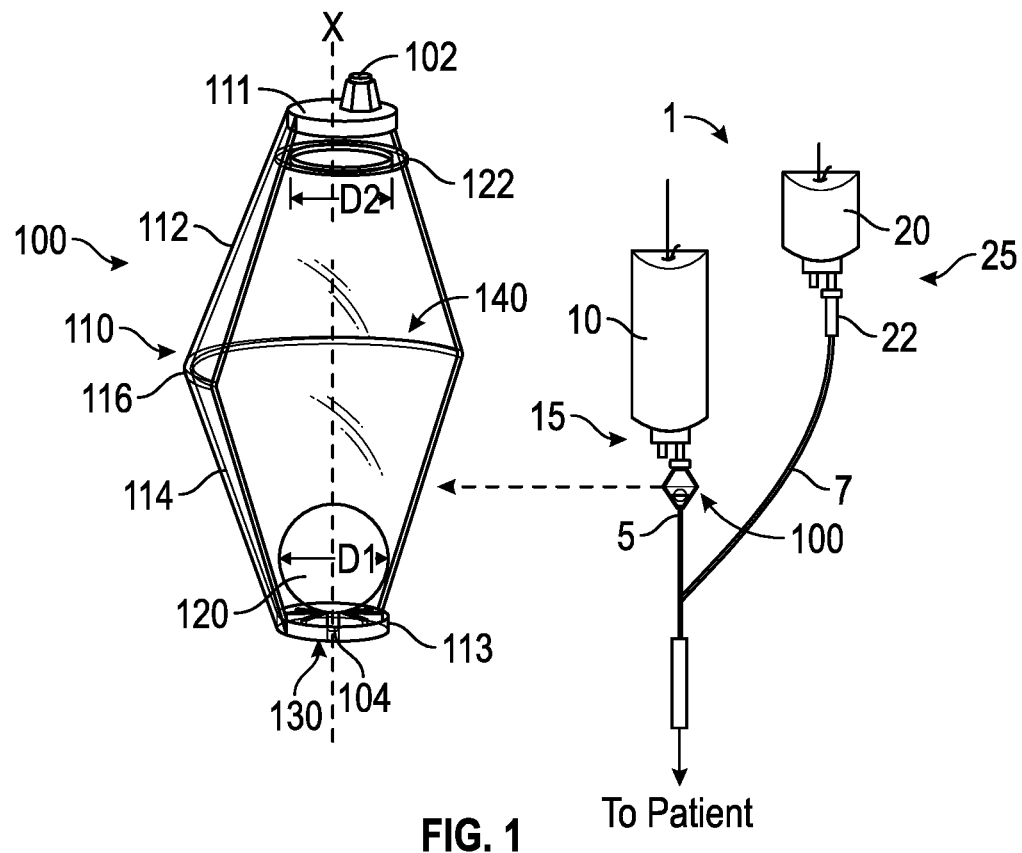
FIG. 1 illustrates an IV extension set that includes a drip chamber device, in accordance with some embodiments of the present disclosure.

FIG. 1 illustrates a multiple line IV extension set 1 that includes a drip chamber device 100 in accordance with some embodiments of the present disclosure. As depicted, IV set 1 includes a primary fluid system 15 and a secondary fluid system 25. An IV pump (optional) may receive fluid from primary fluid system 15 and secondary fluid system 25 via a primary IV fluid line 5 and a secondary IV fluid line 7, and may control and dispense the fluids therefrom to a patient.

In some embodiments, primary fluid system 15 may include a primary fluid source or container such as a primary intravenous (IV) fluid bag 10, which may include or contain a first medical fluid, e.g., saline solution or other medicinal fluid or drug to be administered to the patient. In accordance with some embodiments, a secondary fluid system 25 may include a secondary fluid source or container such as a secondary IV fluid bag 20, which may contain a second medical fluid, e.g., drugs or other secondary fluid to be supplied to the patient for treatment. In some embodiments, the second medical fluid may be different from the first medical fluid. However, the various embodiments of the present disclosure are not limited to the aforementioned configuration. In other embodiments, the first and second fluids may be the same.

According to various embodiments of the present disclosure, as illustrated in FIG. 1, primary IV fluid bag 10, which holds a primary fluid is positioned at a lower axial position or height than the secondary IV fluid bag 20. For example, the primary IV fluid bag 10 may be hung on a suspension system or hanger and then the secondary IV fluid bag 20 may be hung above the primary IV fluid bag and may be coupled to the secondary fluid line 7, which may be connected to the primary fluid line 5 via a connector (e.g., a y-site connector).

Figure 2A:
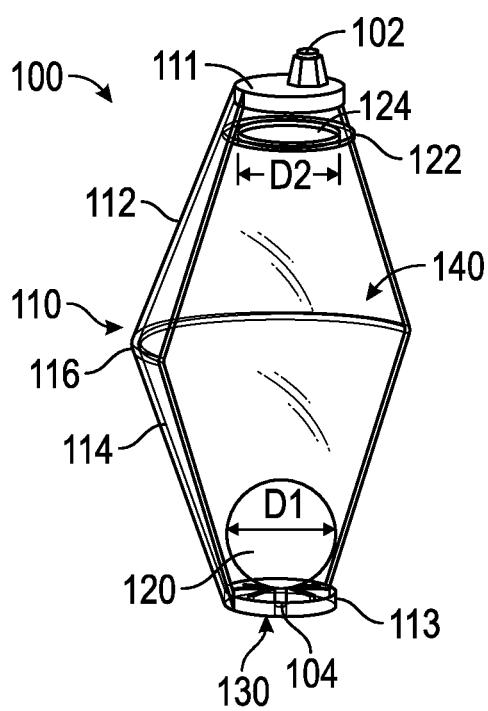
FIG. 2A illustrates a perspective view of a drip chamber device, in accordance with some embodiments of the present disclosure.
Figure 2B:
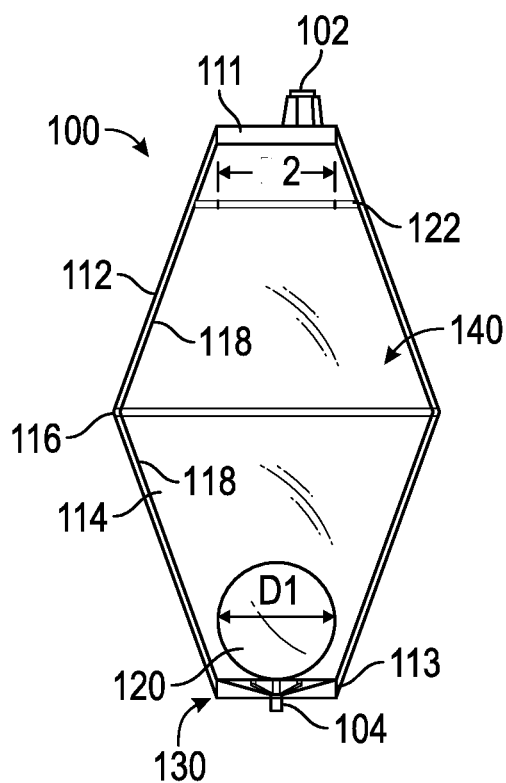
FIG. 2B illustrates a front view of the drip chamber device of FIG. 2A, in accordance with some embodiments of the present disclosure.

FIG. 2A illustrates a perspective view of a drip chamber device 100, in accordance with some embodiments of the present disclosure. FIG. 2B illustrates a front view of the drip chamber device 100 of FIG. 2A, in accordance with some embodiments of the present disclosure. As illustrated, the drip chamber device 100 may have a top end 111 including an inlet 102 for receiving a primary fluid, an opposing bottom end 113 including an outlet 104 for dispensing fluid from the housing 110, and an intermediate section 116 positioned between the top and bottom ends 111 and 113 of the housing 110. The housing 110 may further include a sidewall extending from the top end 111 to the bottom end 113 of the housing 110. For example, in some embodiments, the sidewall may include a first sidewall or sidewall portion 112 and a second sidewall or sidewall portion 114. The first sidewall or sidewall portion 112 and the second sidewall or sidewall portion 114 may define an inner circumferential surface 118 of the housing.

As depicted in FIGS. 2A and 2B, the first sidewall or sidewall portion 112 may extend radially outward and distally from the top end 111 of the housing 110. Similarly, the second sidewall or sidewall portion 114 may extend radially inward and distally from the first sidewall or sidewall portion 112 to the bottom end 113 of the housing 110. In particular, the first sidewall or sidewall portion 112 may extend radially outward from the top end 111 of the housing 110 to the intermediate section 116 of the housing 110. The second sidewall or sidewall portion 114 may extend radially inward from the intermediate section 116 to the bottom end 113 of the housing 110. In a similar manner, the second sidewall or sidewall portion 114 may extend radially outward and proximally from the bottom end 113 of the housing 110 to the intermediate section 116 of the housing. The first sidewall or sidewall portion 112 may extend radially inward and proximally from the intermediate section 116 of the housing 110 to the top end of the housing 111.

Accordingly, each of the first sidewall or sidewall portion 112 and the second sidewall or sidewall portion 114 may have a conical shape. The housing 110 may thus in some embodiments have a diamond shape. However, the various embodiments of the present disclosure are not limited to the aforementioned configuration. In other embodiments, the housing may have an oblong or oval shape, or any other shape where the top and bottom ends 111 and 113 are symmetrically disposed with respect to each other and the intermediate section 116 is disposed radially outward with respect to the first and second ends 111 and 113.

Accordingly, the drip chamber device 100 may be referred to as a convergent-divergent drip chamber device based on the shape of the housing where the first sidewall or sidewall portion 112 extends radially outward (i.e., diverges) from the top end 111, and the second sidewall or sidewall portion 114 extends radially inward (i.e., converges) from the first sidewall or sidewall portion 112. The convergent-divergent conical shape of the drip chamber device may provide several advantages, as shall be discussed in further detail below.

In accordance with various embodiments of the present disclosure, the inner circumferential surface 118 of the housing 110 may define a chamber 140, which fluidly connects the inlet 102 with the outlet 104. As depicted in FIGS. 2A and 2B, with continued reference to FIG. 1, the drip chamber device 100 may further include a valve member 120 movably disposed in the chamber 140. As shall be described in further detail below, based on a level of fluid within the chamber 140, valve member 120 may be configured to move between (i) a closed state where fluid communication between the inlet 102 and the chamber 140 is blocked, and (ii) an open state where fluid communication between the inlet 102 and the chamber 140 is not blocked.

In some embodiments, the valve member 120 may be a spherical ball or disc. In other embodiments, valve member 120 may be an oblong or oval ball or disc. The valve member 120 may be a solid body or hollow ball having a density less than the density of the primary fluid, the secondary fluid, or a combination of the primary and secondary fluids in the chamber 120. Accordingly, the valve member having the lesser density will float on the fluid 142 in the chamber which has a higher density. Since the fluid 142 in the chambers has the higher density, the fluid 142 may exert a buoyant force on the valve member 120, causing it to move upwards (proximally) as the level of the fluid in the chamber continues to rise. In some embodiments, the valve member 120 may be formed of a material including at least one of Isoprene rubber, polyethylene (PE) foam, ethylene propylene diene monomer (EPDM) foam, or any other material having a density less than the density of the primary fluid, the secondary fluid, or a combination of the primary and secondary fluids in the chamber.

According to various embodiments of the disclosure, the drip chamber device 100 may further include a sealing ring 122 having a hollow interior 124 for accommodating and engaging the valve member 120 in order to block fluid in the chamber 140 from flowing into the IV bag 10, which would otherwise cause underinfusion of the secondary fluid to the patient. As depicted, the sealing ring 122 may be circumferentially disposed on the inner circumferential surface 118 of the housing 110. In some embodiments, the sealing ring 122 may be disposed adjacent to and distally from the top end 111 of the housing 110. For example, the sealing ring may be positioned on the inner circumferential surface 118 at a distance from the top end 111 that is greater than or equal to the radius of the valve member, e.g., spherical ball 120.

As depicted, the inner diameter D2 of the sealing ring 122 may be substantially equal to the diameter D1 of the valve member 120. For example, the inner diameter D2 of the sealing ring 122 may be equal to or less than the diameter D1 of the valve member 120 to allow valve member 120 to be accommodated and press-fit or interference-fit therein. Although the sealing ring 122 is illustrated as having a flat or planar profile, the various embodiments of the present disclosure are not limited to the aforementioned configuration. For example, in some embodiments the sealing ring 122 may have a shape that tapers upwards (proximally) so as to direct or otherwise guide the valve 120 towards the inner diameter D2 of sealing ring 122 and the central axis X (illustrated in FIG. 1).

Accordingly, the valve member 120 may be securely accommodated in the sealing ring 122 with the maximum of the diameter D1 of the valve member 120 forming an interference fit or a press fit with the inner diameter D2 of the sealing ring 122. As shall be described in further detail below, the valve member 120 being securely accommodated or fit in the sealing ring 122 produces a closed state in which fluid communication between the inlet 102 and the chamber 140 is blocked. Accordingly, fluid in the chamber 140 may be prevented from otherwise flowing into the primary IV bag 10 via the inlet 102. Advantageously, secondary fluid having entered the chamber 140 may be prevented from entering primary IV fluid bag 10 and causing a situation where insufficient secondary fluid is delivered to the patient (under infusion). Further, the aforementioned configuration of the drip chamber device including valve member 120 and sealing ring 122 may also be advantageous in preventing delay of administration of the secondary fluid (which would have otherwise entered the primary IV bag 10) to the patient. As shall also be described in further detail below, in the open state the valve member 120 may be disposed outside of the sealing ring 120, thereby allowing fluid communication between the inlet 102 and the outlet 104.

Figure 2C:
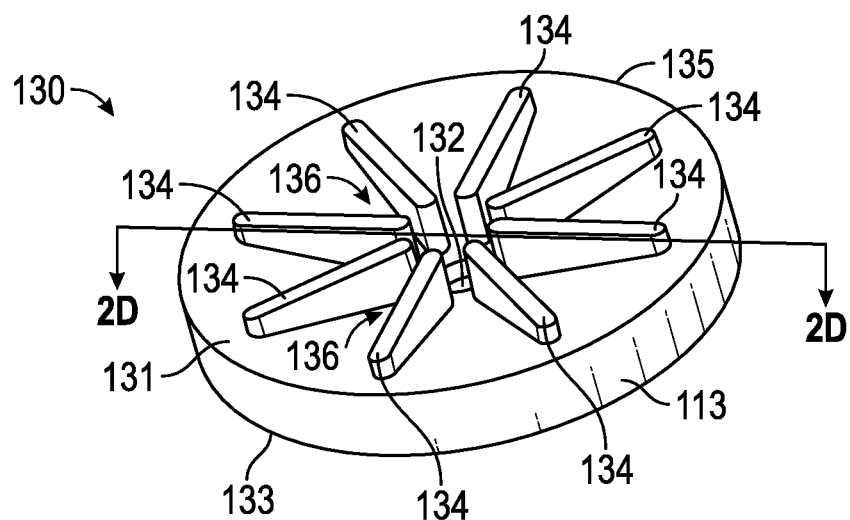
FIG. 2C illustrates a perspective view of a base plate of the drip chamber device of FIG. 2A, in accordance with some embodiments of the present disclosure.
Figure 2D:
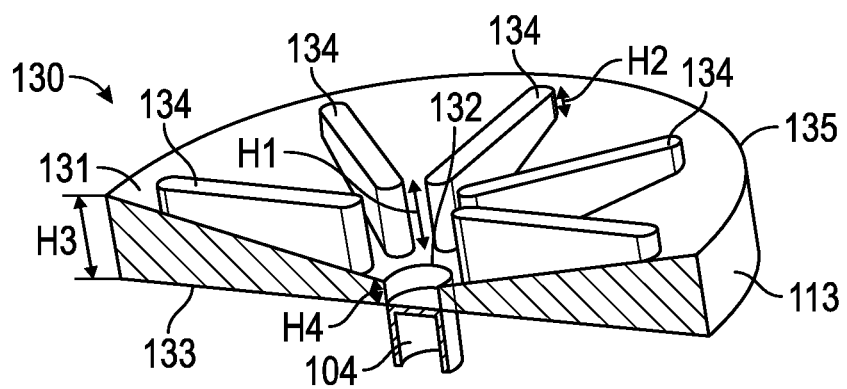
FIG. 2D illustrates a cross-sectional view of the base plate of FIG. 2C along line 2D-2D, in accordance with some embodiments of the present disclosure.

FIG. 2C illustrates a perspective view of a base plate 130 of the drip chamber device 100 of FIG. 2A, in accordance with some embodiments of the present disclosure. FIG. 2D illustrates a cross-sectional view of the base plate 130 of FIG. 2C along line 2D-2D, in accordance with some embodiments of the present disclosure. As depicted in FIGS. 2C and 2D with continued reference to FIGS. 1, 2A, and 2B, the bottom end 113 of the housing 110 may include the base plate 130 on which the valve member 120 may be seated in the open state. The base plate 130 may have a top surface 131, a bottom surface 133, and a plurality of valve support members 134 protruding proximally and longitudinally from the top surface 131 of the base plate.

As further depicted, the base plate 130 may include an aperture 132 extending from the top surface 131 through the bottom surface 133 of the base plate 130. The aperture 132 may fluidly communicate the chamber 140 with the outlet 104. The valve support members 134 may be radially spaced apart about a central longitudinal axis X of the drip chamber device. In particular, valve support members 134 may be radially spaced apart about the aperture 132. Each spacing between adjacent valve support members may define a flow guide portion 136 through which fluid exiting the chamber 140 flows into the outlet 104 via aperture 132. The aforementioned configuration of the valve support members 134 protruding from the top surface is advantageous in that in the open state where fluid flows from the chamber 140 into the outlet 104, the valve member 120 may be seated and supported on the valve support members at a height H1 above the aperture 132. Accordingly, fluid flow into the outlet via the chamber 140 may not be occluded or otherwise interfered with by the valve member 120 seated above the aperture 132.

According to various embodiments of the present disclosure, the top surface 131 of the base plate 130 may be a ramped surface, which is angled and tapers radially inward from an outer periphery 135 of the base plate 130 to the aperture 132 of the base plate 130. In particular, as illustrated in FIG. 2D, the base plate 130 may taper from a height H3 at the outer periphery 135 to a height H4 at the aperture 132. The aforementioned configuration of the ramped or tapered structure of the base plate 130 may be advantageous in providing a downwardly (distally) inclined surface along which fluid in the chamber may flow along and be guided into the aperture 13.

Figure 3A:
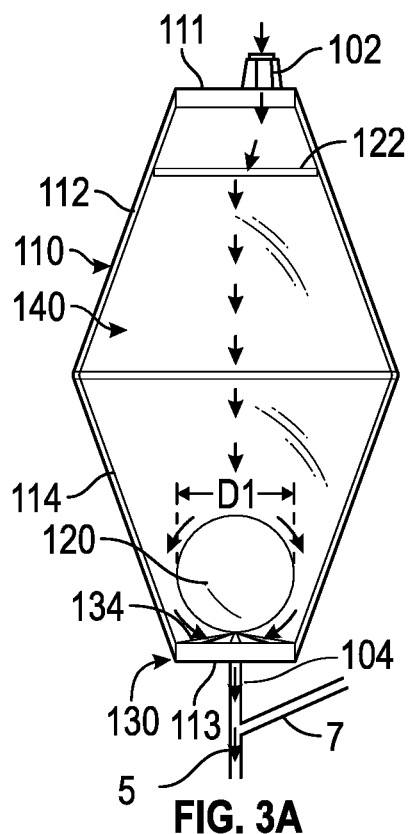
FIG. 3A illustrates an operational state of a drip chamber device when a primary fluid flows into the drip chamber device, in accordance with some embodiments of the present disclosure.

FIG. 3A-3D illustrate operational states of a drip chamber device 100, in accordance with some embodiments of the present disclosure. FIG. 3A illustrates an operational state of the drip chamber device 100 when a primary fluid flows into the drip chamber device 100. As depicted, the valve member 120 is seated on the valve support members 134 at the raised position relative to the aperture 132 (illustrated in FIGS. 2C and 2D). In this position, the open state, fluid may flow from the primary IV bag 10 into the chamber 140 via the inlet 102 as illustrated by the arrows. Once the primary fluid enters the chamber, the primary fluid may flow onto the top surface 131 of base plate 130. Due to the ramped, angled, or inclined structure of the base plate 130, the fluid may be guided or urged to flow down the inclined surface of the base plate 130 and into the outlet 104 via the aperture 132. The spacings between adjacent valve support members that define flow guide portions 136 may further assist in guiding the primary fluid towards the aperture 132.

Figure 3B:
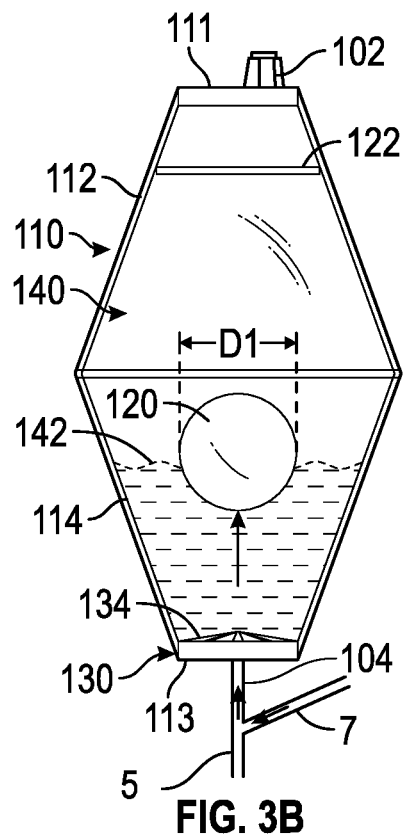
FIG. 3B illustrates an operational state of the drip chamber device where secondary fluid backflows into the drip chamber device from a secondary fluid line, in accordance with some embodiments of the present disclosure.

FIG. 3B illustrates an operational state of the drip chamber device 100 where secondary fluid backflows into the primary fluid line 5 and the drip chamber device 100 from the secondary fluid line 7. As depicted, as the secondary fluid enters and collects in the drip chamber device 100, the secondary fluid may exert a buoyant force F on the valve member 120. When the buoyant force F exceeds a downward force applied to the fluid by the weight of the valve member 120, the valve member 120 may be translated or otherwise moved proximally (upstream or upwards) towards the top end 111 of the housing 110.

Figure 3C:
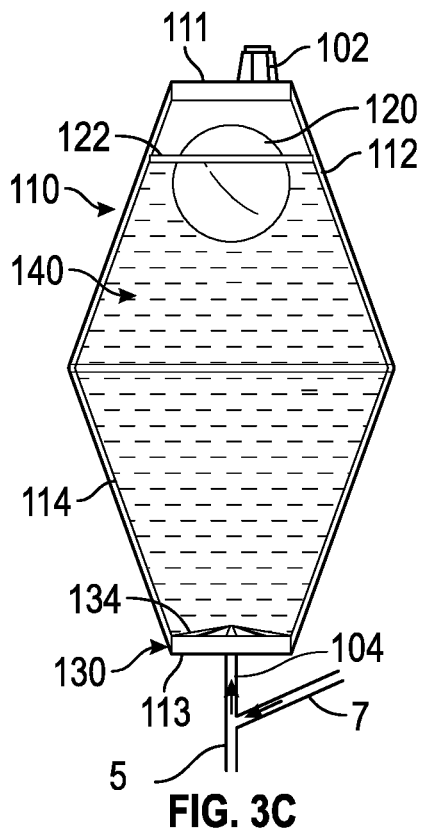
FIG. 3C illustrates an operational state of the drip chamber device of FIG. 3B where secondary fluid backflow into the drip chamber device continues until fluid in the drip chamber reaches a predetermined level and the buoyant force on the valve member engages the valve member in the sealing ring to block fluid flow from the chamber to the inlet in accordance with some embodiments of the present disclosure.

FIG. 3C illustrates an operational state of the drip chamber device of FIG. 3B where secondary fluid backflow into the drip chamber device continues until fluid in the drip chamber reaches a predetermined level and the buoyant force on the valve member engages the valve member in the sealing ring to block fluid flow from the chamber to the inlet in accordance with some embodiments of the present disclosure. As depicted, as the secondary fluid continues to backflow into the primary fluid line 5, the level of the fluid in the chamber 140 continues to rise until it reaches a predetermined level where the buoyant force pushes the valve member 120 into the sealing ring 122. Since the diameter D1 of the valve member 120 is greater than or equal to the inner diameter of the sealing member 122, the valve member forms an interference fit or a press fit in the sealing ring 122. Accordingly, fluid in the chamber 140 is obstructed or otherwise blocked from rising above the level of the sealing member 122, and thereby prevented from entering the inlet 102 and the IV bag 10. As such, the structure of the drip chamber device 100 as described herein is advantageous in preventing secondary fluid from entering the primary IV bag 10 and resultantly being underinfused to the patient. Furthermore, the convergent-divergent conical shape of the housing 110 is advantageous in that the walls of inner circumferential surface 118 guide motion of the valve member as it is translated proximally toward the top surface by the buoyant force. In particular, the first sidewall or sidewall portion 112 having the conical shape extending radially inward from the intermediate section 116 of the housing and tapering at the top end 111 may guide the path of the valve member 120 towards the sealing ring 122 and the central axis X (illustrated in FIG. 1). Accordingly, the conical shape of the housing 110 is advantageous in ensuring that the valve member 120, when subject to the buoyant force F and travels proximally towards the top end, may be guided towards the central portion of the chamber 140 where the sealing ring 122 is disposed.

Figure 3D:
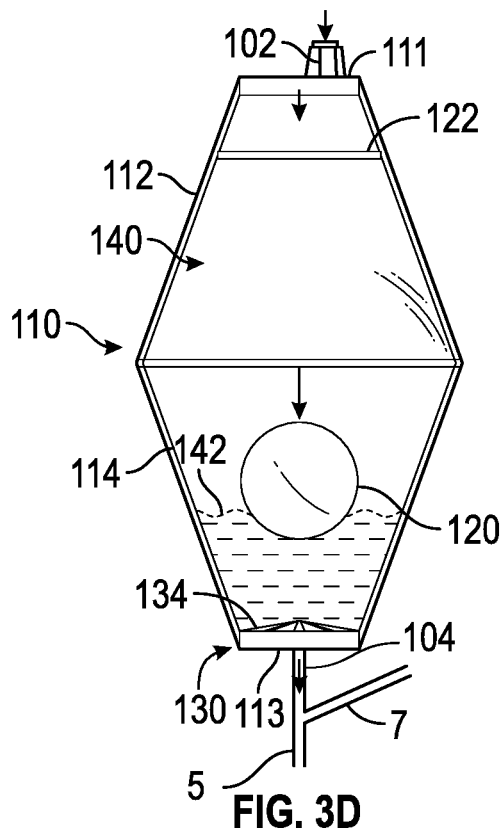
FIG. 3D illustrates an operational state of the drip chamber device where secondary fluid backflow into the drip chamber device has ceased and the fluid in the drip chamber falls below the predetermined level, in accordance with some embodiments of the present disclosure.

FIG. 3D illustrates an operational state of the drip chamber device 100 where secondary fluid backflow into the drip chamber device 100 has ceased and the fluid in the drip chamber falls below the predetermined level, in accordance with some embodiments of the present disclosure. As depicted, as the secondary fluid ceases to backflow into the primary fluid line 5 and collect in the drip chamber device 100, the level of the fluid in the chamber may decrease below the predetermined level. As the level of the fluid decreases, the buoyant force on the valve member is diminished and the valve member, with its mass subject to gravity forces may fall distally (downstream or downwards) until a point where the valve member is seated on the base plate as illustrated in FIG. 3A Accordingly, the various embodiments of the present disclosure are advantageous in providing a drip chamber device capable of preventing under-infusion of the secondary drug by blocking the secondary drug from entering into the primary IV bag 10, as discussed previously. The drip chamber device of the various embodiments described herein is further advantageous as it minimizes the number of separate components of an IV set by replacing a check valve and a conventional drip chamber with the drip chamber device. As a result, cost of the IV set may be reduced. Additionally, the various embodiments of the present disclosure are advantageous in providing a drip chamber device which provides better sealing as the fluid level in the housing increases. Further advantageously, the drip chamber device of the various embodiments described herein may optionally be retrofit with existing IV pump devices, so there is no need for specialized components in order to make the drip chamber device compatible with existing pumps.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber device, comprising:
   a housing having a top end including an inlet, and a bottom end including an outlet disposed downstream of the inlet;
   a chamber defined by an inner circumferential surface of the housing, and fluidly connecting the inlet with the outlet, the inner circumferential surface having a sealing ring, disposed distally to the inlet, a first sidewall extending radially outward and distally from the top end of the housing, and a second sidewall extending radially inward and distally from the first sidewall to the bottom end of the housing; and
   a valve member disposed in the chamber to move between (i) a closed state where fluid communication between the inlet and the chamber is blocked by engagement of the valve member against the sealing ring, and (ii) an open state where the valve member is spaced apart from the sealing ring in a direction distal to the inlet, based on a level of fluid within the chamber, such that fluid communication between the inlet and the chamber is not blocked.

2. The drip chamber device of claim 1, wherein each of the first and second sidewalls comprises a conical shape.

3. The drip chamber device of claim 1, wherein the sealing ring is circumferentially disposed on the inner circumferential surface along the first sidewall.

4. The drip chamber device of claim 1, wherein the valve member comprises a spherical ball.

5. The drip chamber device of claim 4, wherein a distance between a top end of the housing and the sealing ring is greater than or equal to a radius of the spherical ball.

6. The drip chamber device of claim 4, wherein an inner diameter of the sealing ring is less than or equal to a diameter of the spherical ball.

7. The drip chamber device of claim 1, wherein the bottom end of the housing comprises a base plate having a top surface, a bottom surface, and a plurality of valve support members protruding proximally from the top surface of the base plate.

8. The drip chamber device of claim 7, wherein the base plate comprises an aperture extending from the top surface through the bottom surface of the base plate, the aperture fluidly communicating the chamber with the outlet.

9. The drip chamber device of claim 8, wherein the top surface of the base plate comprises a ramped surface which is angled and tapers radially inward from an outer periphery of the base plate to the aperture of the base plate.

10. The drip chamber device of claim 7, wherein the valve support members are radially spaced apart about a central longitudinal axis of the drip chamber device.

11. A drip chamber device, comprising:
a housing having a top end including an inlet for receiving a primary fluid, an opposing bottom end including an outlet for dispensing fluid from the housing, an intermediate section between the top end and the bottom end, and a sidewall having (i) a first portion extending radially outward from the top end to the intermediate section of the housing, and (ii) a second portion extending radially inward from the intermediate section to the bottom end of the housing, wherein an inner circumferential surface of the sidewall defines a chamber;
a sealing ring circumferentially disposed along the first portion of the inner circumferential surface; and
a valve member moveably disposed in the chamber, the valve member being displaceable in a proximal direction into the sealing ring by a buoyant force when fluid level in the chamber exceeds a predetermined level.

12. The drip chamber device of claim 11, wherein each of the first and second portion of the sidewall comprises a conical shape.

13. The drip chamber device of claim 11, wherein the sealing ring is disposed adjacent to and distally from the top end of the housing at a distance greater than or equal to a radius of the valve member.

14. The drip chamber device of claim 11, wherein the valve member comprises a spherical ball.

15. The drip chamber device of claim 14, wherein an inner diameter of the sealing ring is less than or equal to a diameter of the spherical ball.

16. The drip chamber device of claim 11, wherein the bottom end of the housing comprises a base plate having an aperture extending axially therethrough, the aperture fluidly communicating the chamber with the outlet.

17. The drip chamber device of claim 16, wherein the base plate further comprises a plurality of valve support members protruding longitudinally from a top surface of the base plate.

18. The drip chamber device of claim 17, wherein the valve support members are radially spaced apart about the aperture, and each spacing between adjacent valve support members defines a flow guide portion through which fluid exiting the chamber flows into the outlet.

19. The drip chamber device of claim 17, wherein the base plate comprises a ramped surface which is angled and tapers radially inward from an outer periphery of the base plate to the aperture of the base plate.

20. A drip chamber device, comprising:
a housing having a top end including an inlet, and a bottom end including an outlet disposed downstream of the inlet;
a chamber defined by an inner circumferential surface of the housing, and fluidly connecting the inlet with the outlet, and the inner circumferential surface having a first sidewall extending radially outward and distally from the top end of the housing, and a second sidewall extending radially inward and distally from the first sidewall to the bottom end of the housing; and
a valve member disposed in the chamber to move between a closed state, where fluid communication between the inlet and the chamber is blocked, and an open state, where fluid communication between the inlet and the chamber is not blocked, based on a level of fluid within the chamber.

* * * * *